US012661271B2

(12) United States Patent
Johannison et al.

(10) Patent No.: US 12,661,271 B2
(45) Date of Patent: Jun. 23, 2026

(54) MEDICAL DRESSING COMPRISING A BACKING LAYER WITH THREE DIMENSIONAL FEATURES

(71) Applicant: Mölnlycke Health Care AB, Gothenburg (SE)

(72) Inventors: Ulf Johannison, Landvetter (SE); Sami Ahsani, Gothenburg (SE); Anders Dahlberg, Olofstorp (SE)

(73) Assignee: Mölnlycke Health Care AB, Mölndal (SE)

( * ) Notice: Subject to any disclaimer, the term of this patent is extended or adjusted under 35 U.S.C. 154(b) by 370 days.

(21) Appl. No.: 17/641,154

(22) PCT Filed: Sep. 10, 2020

(86) PCT No.: PCT/EP2020/075328
§ 371 (c)(1),
(2) Date: Mar. 8, 2022

(87) PCT Pub. No.: WO2021/048278
PCT Pub. Date: Mar. 18, 2021

(65) Prior Publication Data
US 2022/0331167 A1 Oct. 20, 2022

(30) Foreign Application Priority Data
Sep. 13, 2019 (EP) ..................................... 19197307

(51) Int. Cl.
A61F 13/0206 (2024.01)
A61F 13/02 (2024.01)
A61F 13/0203 (2024.01)

(52) U.S. Cl.
CPC ...... *A61F 13/0206* (2013.01); *A61F 13/0226* (2013.01); *A61F 13/0276* (2013.01)

(58) Field of Classification Search
CPC .... A61F 13/00; A61F 13/021; A61F 13/0206; A61F 13/0226; A61F 13/0276; A61F 13/0246; A61F 13/025; A61F 13/02; A61F 13/0203; A61F 2013/00089; A61F 2013/00582
USPC .............................. 602/41–43, 47, 52, 54, 58
See application file for complete search history.

(56) References Cited

U.S. PATENT DOCUMENTS

| | | | |
|---|---|---|---|
| 10,828,203 | B2 | 11/2020 | Ahsani et al. |
| 2004/0087884 | A1 | 5/2004 | Haddock et al. |
| 2005/0059918 | A1 | 3/2005 | Sigurjonsson et al. |
| 2014/0142523 | A1 | 5/2014 | Steinbaugh et al. |

(Continued)

FOREIGN PATENT DOCUMENTS

| | | | | |
|---|---|---|---|---|
| CN | 1756519 A | 4/2006 | | |
| DK | 1675536 T3 * | 4/2016 | ........... | A61L 15/425 |

(Continued)

OTHER PUBLICATIONS

JP 2008220633 machine translation (Year: 2008).*

(Continued)

*Primary Examiner* — Caitlin A Carreiro
(74) *Attorney, Agent, or Firm* — Ballard Spahr LLP

(57) ABSTRACT
Described is a medical dressing having a backing layer containing three dimensional features. The dressing is flexible and has an improved wear time. Also described is a method for preparing such a medical dressing.

15 Claims, 6 Drawing Sheets

(56) References Cited

U.S. PATENT DOCUMENTS

| | | | | |
|---|---|---|---|---|
| 2014/0154459 A1* | 6/2014 | Krautkramer | ......... | A61F 13/622 |
| | | | | 428/99 |
| 2018/0289552 A1 | 10/2018 | Caneppele | | |

FOREIGN PATENT DOCUMENTS

| | | | | | | |
|---|---|---|---|---|---|---|
| EP | 0768071 | A1 | 4/1997 | | | |
| EP | 2491905 | A1 | 8/2012 | | | |
| JP | 2004160220 | | 6/2004 | | | |
| JP | 2008220633 | A | * | 9/2008 | ........... | A61M 25/02 |
| JP | 2018513744 | | 5/2018 | | | |
| JP | 2020163038 | | 10/2020 | | | |
| WO | WO-0250176 | A1 | * | 6/2002 | ......... | A61F 13/0203 |

OTHER PUBLICATIONS

International Search Report and Written Opinion were mailed on Nov. 19, 2020 by the International Searching Authority for International Application No. PCT/EP2020/075328 filed on Sep. 10, 2020 and published as WO 2021048278 (Applicant—Molnlycke Health Care AB) (10 pages).

* cited by examiner

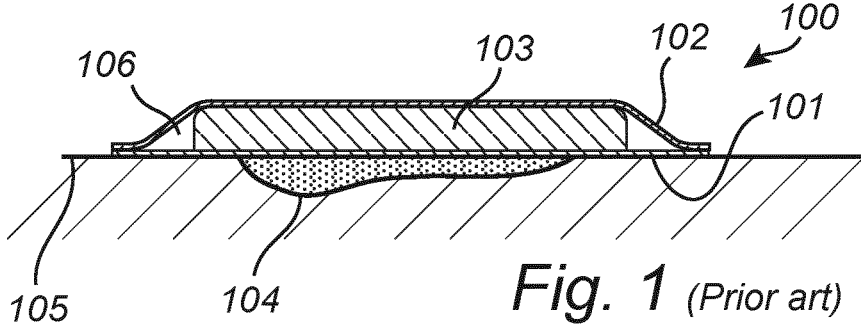
*Fig. 1* (Prior art)
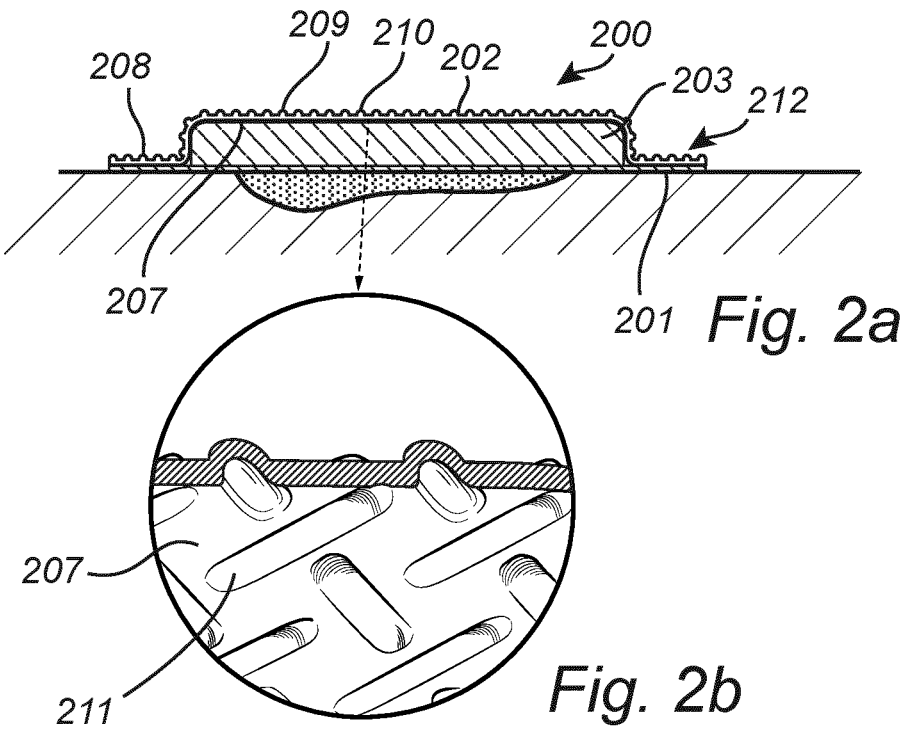
*Fig. 2a*
*Fig. 2b*

Δ evaporation vs reference as function of time

—●— Dressing G
—▲— Dressing F
·········· Log. (Dressing G)
- - - - Log. (Dressing F)

MEDICAL DRESSING COMPRISING A BACKING LAYER WITH THREE DIMENSIONAL FEATURES

CROSS-REFERENCE TO RELATED APPLICATIONS

This application is a U.S. National Phase Application of International Application No. PCT/EP2020/075328, filed Sep. 10, 2020, which claims priority to European Application No. 19197307.2, filed Sep. 13, 2019, each of which are hereby incorporated by reference in their entirety.

TECHNICAL FIELD

The present disclosure generally relates to a medical dressing comprising a backing layer comprising three dimensional features. The present disclosure also relates to a method for preparing such a dressing.

BACKGROUND

Adhesive medical dressings are frequently used in wound care, both for the purpose of treating wounds and scars and for the purpose of preventing these from occurring in the first place.

One problem with adhesive dressings is their tendency to lose the adhesive connection to the skin of a wearer. When the dressing is applied to a body part that moves (e.g. at joints) and/or rubs against clothing or objects, the dressing may become partially or, in worst case, fully detached from the skin. Even partial detachment can compromise the function of the dressing, since compartments for body fluids between the skin and the adhesive skin surface of the dressing may be formed. As fluid accumulates, the compartments grow, and the wear time of the dressing is impaired. A detached dressing is difficult to re-apply, so the dressing typically needs to be replaced with a new dressing, which can be costly.

The wear time may be particularly problematic for convex body parts, such as heels, knees and elbows, which may be referred to as "hard to dress-areas". Some dressings, typically referred to as "border dressings" comprise an absorbent pad, a backing layer and, an adhesive skin contact layer. The backing layer and, optionally, the adhesive skin contact layer extend peripherally beyond the pad to form a border portion. A border dressing is attached to the skin at the adhesive borders, or at the entire surface of the skin facing layer of the dressing.

For border dressings, detachment of the dressing may initiate at the edges of the absorbent pad. As a patient moves or bends, the backing layer is subjected to tension and extends obliquely from the pad, which is generally much thicker than the backing layer (and the skin contact layer). This way, air pockets may form around the edges of the pad. As the backing layer is stretched, the air pockets increase, leading to detachment of the dressing from the skin. Accumulation of fluids in the air pockets further impairs the wear time of the dressing.

The mechanical tension on the backing layer may also cause shear stresses on the adhesive skin contact layer, that in turn results in detachment.

In view of the above, there is a need for a medical dressing, which is flexible and provides for an improved wear time.

SUMMARY

In view of the above mentioned and other drawbacks of the prior art, it is an object of the present disclosure to provide improvements with respect to medical dressings, particularly with respect to improving the wear time and flexibility.

According to a first aspect of the present disclosure, there is provided a medical dressing comprising an adhesive skin contact layer and a backing layer, wherein the backing layer has a first surface facing the skin contact layer and an opposing second surface, wherein the backing layer comprises a plurality of three dimensional features forming protrusions on the second surface of the backing layer and depressions on the first surface of the backing layer.

The present inventive concept is based on the insight that the flexibility of a medical dressing also poses demands on the backing layer of the dressing. The backing layer needs to conform with the movement of the body, and endure the stress applied during stretching of the dressing.

The three dimensional features form extra material sections of the backing layer, and allow the backing layer to be stretched, e.g. due to bending of a knee, to a higher degree than if the backing layer was essentially flat. When the wearer moves and the dressing is stretched, the three dimensional features flatten out to conform to the movement of the wearer.

In embodiments, the skin contact layer is substantially planar.

In other words, the skin contact layer is a flat layer. The skin contact layer does not follow the contour of the three dimensional features of the backing layer, i.e. it does not follow the depressions formed in the first surface of the backing layer. Instead, it remains adherent to the skin of the wearer. This is beneficial since a pleated or protruded skin contact layer could give rise to liquid leakage, and detachment of the dressing from the skin.

In embodiments, the medical dressing further comprises an absorbent pad arranged between the backing layer and the adhesive skin contact layer, wherein the backing layer and the adhesive skin contact layer extend around the periphery of the absorbent pad.

The inventive concept is particularly beneficial for border dressings comprising an absorbent pad. As mentioned hereinbefore, gaps may form around the edges of the pad, which is typically thicker than the backing layer and the skin contact layer. The backing layer of the present disclosure conforms more easily to the edges of the pad and minimizes the gaps formed around the pad.

In embodiments, the first surface of the backing layer is not adhesively attached to the skin contact layer or the absorbent pad, if present, in the areas forming the depressions.

That is, the depressions formed in the first surface of the backing layer are substantially free from contact with the underlying skin contact layer or, if present, absorbent pad. This enables expansion of the backing layer as the dressing (and the wearer) stretches or moves.

The three dimensional features may be arranged in a discrete or continuous pattern across at least a portion of the backing layer.

For example, the three dimensional features may be formed in a zig-zag, grid or wave pattern extending across the surface of the backing layer. Alternatively, the three dimensional features are arranged in a discrete pattern across the surface of the backing layer. For example, a pattern of circular, oval, rectangular, elliptical, diamond or bean shaped three dimensional features may be envisioned.

The pattern of three dimensional features also has the advantage of improving the visual appearance of the dressing.

In embodiments, the pattern of three dimensional features extends over at least 30%, preferably at least 70%, and more preferably at least 90% of the surface area of the backing layer.

It is beneficial to have the patterned backing layer across as much surface as possible of the backing layer (and the dressing), not only at the border or at the central portion, to maximize the flexibility of the entire dressing.

In embodiments, the dressing has a longitudinal (y) direction and a lateral (x) direction, and the three dimensional features are arranged to extend in at least one of, preferably both of, the longitudinal (y) and the lateral (x) directions.

The three dimensional features may be arranged to extend only, or substantially more, in the longitudinal (y), or lateral (x) directions. This may be beneficial if one would want to selectively steer the flexibility or stretching ability of the dressing in one particular direction.

To maximize flexibility, and wear time, the three dimensional features may be arranged to extend in both of the longitudinal (y) and the lateral (x) directions. The dressing is thereby flexible in both directions regardless of how the dressing is applied to a body part.

In embodiments, the three dimensional features have a height of between 0.3 and 10 mm, preferably between 0.5 and 5.0 mm, more preferably between 0.8 and 3.0 mm These dimensions leave sufficient extra backing layer material that can expand as the dressing and the body part stretches.

The height of the three dimensional features may be varied depending on the desired degree of stretchability. The height is also dependent on the thickness of the backing layer. For example, for a thicker backing layer, the height of the three dimensional features may be higher, whereas for a thinner backing layer, the height may be lower.

In embodiments, the backing layer has a non-uniform thickness.

Accordingly, the backing layer comprises zones that are thinner than the remaining parts of the backing layer. This has the effect that the stretching ability of the backing material is improved, and thereby also the wear time. Furthermore, the breathability of the dressing is improved.

In embodiments, each three dimensional feature comprises a top portion, and at least one slope portion, wherein the thickness of the backing layer in the top portion of the three dimensional feature is higher than in the at least one slope portion of the three dimensional feature.

Accordingly, the backing material in the slopes of each protrusion is thinner. This enhances the ability of the backing layer to stretch while also enhancing the breathability of the backing layer, and the dressing.

It also has the effect that the backing layer better conforms to the edges of the pad and minimizes gap formation around such edges.

In embodiments, the slope portion is at least 10% thinner, preferably at least 20% thinner, and more preferably at least 30% thinner than the top portion of the three dimensional features.

In order to further enhance the flexibility of the dressing, and thereby the wear time, the absorbent pad may comprise a plurality of cuts extending at least partly through the absorbent pad.

According to second aspect of the present disclosure, there is provided a method for forming a backing layer for a medical dressing; the backing layer comprising a plurality of three dimensional features, wherein the method comprises:

providing a backing layer forming a plurality of three dimensional features in said backing layer by:

a) heating said backing layer to a temperature between 100 and 200° C., preferably between 140 and 180° C. and b) contacting a first surface of said backing layer with a molding tool having a surface comprising a pattern of three dimensional structures.

According to a third aspect of the present disclosure, there is provided a method for forming a medical dressing comprising:

providing a backing layer comprising a plurality of three dimensional features, arranging the backing layer on an adhesive skin contact layer, optionally arranging an absorbent pad between the backing layer and the skin contact layer, wherein the backing layer has a first surface facing the skin contact layer and an opposing second surface, and wherein the plurality of three dimensional features are formed by a) heating the backing layer to a temperature between 100 and 200° C., preferably between 140 and 180° C. and b) contacting the first surface of the backing layer with a molding tool having a surface comprising a pattern of three dimensional structures.

The backing layer is first heated to a temperature close to its melting point, and then subjected to a structured surface of the molding tool to form protrusions in the backing layer. The structured surface of the molding tool correspond to the pattern of three dimensional features to be formed in the backing layer.

Step b) is preferably performed at a temperature between 10 and 50° C., preferably between 20 and 40° C. This is to cure the backing layer and affix the pattern of three dimensional features in the backing layer.

The pattern of three dimensional features form depressions on the surface of the backing layer that is to contact the skin contact layer, and the absorbent pad, if present, when assembled, and protrusions on the opposing (second) surface of the backing layer (the outermost surface of the dressing).

In embodiments the method further comprises the step of stretching the backing layer by applying vacuum to the backing layer.

The application of vacuum allows the backing layer to be stretched, and to provide a non-uniform thickness in the backing layer.

Preferably step b) and step c) are performed simultaneously.

This way, vacuum is applied simultaneously with contacting the backing layer with a structured mold. Accordingly, the pattern of three dimensional pattern becomes fixed and stretched simultaneously. This also results in that the slopes of the three dimensional features become thinner than the top of the protrusion.

Further features of, and advantages with, the present disclosure will become apparent when studying the appended claims and the following description. The skilled addressee realizes that different features of the present disclosure may be combined to create embodiments other than those described in the following, without departing from the scope of the present disclosure.

BRIEF DESCRIPTION OF THE DRAWINGS

The various aspects of the present disclosure, including its particular features and advantages, will be readily understood from the following detailed description and the accompanying drawings, in which:

FIG. 1 illustrates a dressing according to the prior art.

FIG. 2a illustrates a dressing according to one embodiment of the present disclosure.

FIG. 2b is a zoomed-in view of the first surface of the backing layer of the dressing in FIG. 2a.

FIG. 3e is a zoomed in-view of the three dimensional features of FIG. 3a.

FIG. 3f is a cross-section of one three dimensional feature of FIG. 3a.

FIG. 4 illustrates a split-view of a dressing according to one embodiment of the present disclosure, wherein the pad is provided with cuts.

DETAILED DESCRIPTION

Figures 3A, 3B, 3C, 3D:
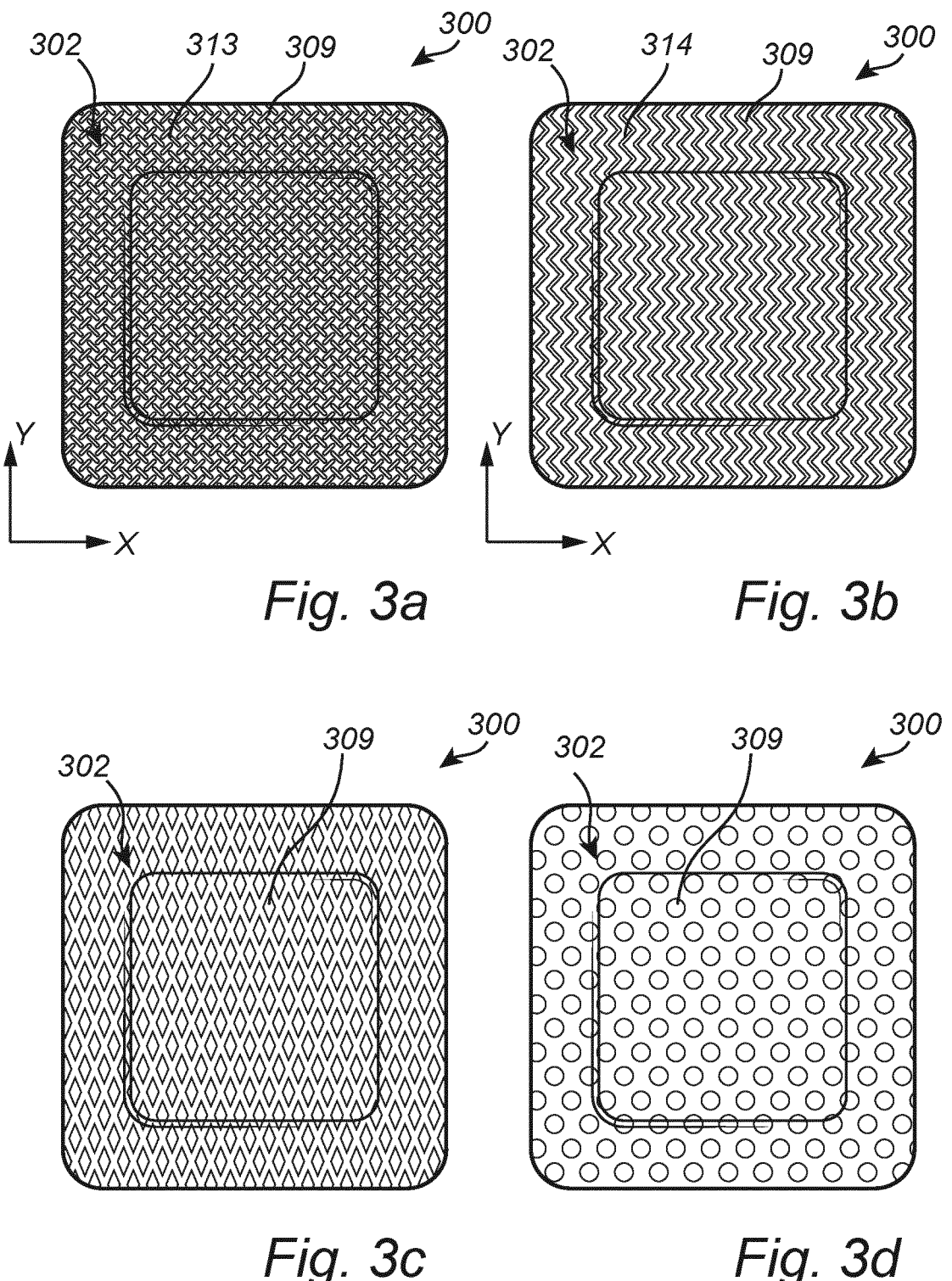
FIGS. 3a-d illustrate top-views of dressings according to four exemplary embodiments of the present disclosure, comprising backing layers with different patterns of three dimensional features.

The present invention will now be described more fully hereinafter with reference to the accompanying drawings, in which currently preferred embodiments of the present invention are shown. The present invention may, however, be embodied in many different forms and should not be construed as limited to the embodiments set forth herein; rather, these embodiments are provided for thoroughness and completeness, and fully convey the scope of the present invention to the skilled person.

FIG. 1 schematically illustrates a dressing 100 according to the prior art. The dressing comprises a wound contact layer 101 and a backing layer 102. A wound pad 103 is arranged between the backing layer 101 and the wound contact layer 102. The dressing is applied to a wound 104 formed on the skin 105 of a wearer.

The dressing according to prior art has a higher tendency to detach from the skin 105 during use due to the formation of annular air pockets or air gaps 106 around the periphery of the wound pad 103. Pressure may build up in such gaps 106 during stretching or movement of the wearer. When a stretching force is applied, the backing layer 102 stretches obliquely from the pad 103 as well as downwards towards the underlying wound contact layer 102, creating a tension to the edges, and thus, detachment typically starts at the edges of the pad 103.

Furthermore, when the dressing is applied to a wearer in vertical position, e.g. on a leg of a person standing, gravitational forces may force the exudate to leak from the wound pad 103 into the gap 106. As fluid accumulates, the detachment of the dressing is further impaired.

FIG. 2 schematically illustrates a dressing 200 according to the present disclosure, comprising an adhesive skin contact layer 201 and a backing layer 202, wherein the backing layer 202 has a first surface 207 facing the skin contact layer 201 and an opposing second surface 208, wherein the backing layer 202 comprises a plurality of three dimensional features 209 forming protrusions 210 on the second surface 208 of the backing layer 202 and depressions 211 on the first surface 207 of the backing layer 202.

As illustrated in FIG. 2, the skin contact layer 201 is substantially planar and adherent to the skin of a wearer.

As used herein, the term "substantially planar" means that the skin contact layer is substantially flat. The skin contact layer is void of protrusions. The skin contact layer is arranged not to follow the contour of the three dimensional features of the backing layer. In other words, the depressions formed in the first surface of the backing layer are not "occupied" by any part of the skin contact layer.

In the embodiment illustrated in FIG. 2, an absorbent pad 203 is arranged between the backing layer 202 and the adhesive skin contact layer 201, wherein the backing layer 202 and the adhesive skin contact layer 201 extend around the periphery of the absorbent pad 203.

Accordingly, a border portion 212 is formed by the adhesive skin contact layer 201 and the backing layer 202 around the pad 203 of the dressing 200.

The absorbent pad 203 is substantially planar. In other words, the absorbent pad 203 is void of protrusions. The pad 203 does not follow the contour of the three dimensional features 209 of the backing layer 202.

The present disclosure is by no means limited to the use of an absorbent pad 203, the advantages associated with the present disclosure are equally applicable to a dressing comprising only a backing layer 202 and a skin contact layer 201.

However, so called "border dressings" are commonly used in the field, and the inventive concept is particularly beneficial for such dressings.

As shown in FIG. 2, the backing layer 202 comprising the three dimensional features 209 is arranged in close proximity to the edges of the absorbent pad 203 such that essentially no, or only a minor gap is formed around the periphery of the pad 203. The backing layer 202 conforms to the thicker pad 203 due to the extra backing layer material provided by the three dimensional features 209. In use, when the wearer and consequently also the dressing moves, the three dimensional features 209 flatten out and extend along with the movement of the wearer. The tension formed near the pad edges is thereby considerably reduced. Accordingly, the risk of detachment is reduced as well as the risk for pressure being built up around the edges of the pad 203.

The backing layer 202 may be partially attached to the skin contact layer 201. The backing layer 202 may be partially attached to the absorbent pad 203, where present. The backing layer 202 may be partially attached to the skin contact layer 201, and to the absorbent pad 203 (if present) in the areas of the backing layer being void of three dimensional features 209.

In alternative embodiments, the backing layer 202 is partially attached to the skin-contact layer 203 in the area forming the border portion 212 of the dressing.

Typically, the first surface 207 of the backing layer 202 is not adhesively attached to the skin contact layer 201 or the absorbent pad 203, if present, in the areas forming the depressions 211.

The small gaps provided by the depressions 211 between the skin contact layer 201, and optionally the absorbent pad 203 and the backing layer 202 allows for the backing layer to be stretched when the dressing (and the patient) moves.

When the backing layer 202 is stretched, the three dimensional features 209 flatten out. During stretching, the gaps formed by the depressions 211 of the first surface 207 will be reduced, and the top portions of the three dimensional features 209 may consequently contact the skin contact layer 201. However, when the dressing 200 returns to its non-stretched mode, this partial adhesive contact will substantially diminish, and the three dimensional features 209 will essentially return to their protruding pattern.

The three dimensional features may be arranged in a discrete or continuous pattern across the backing layer as illustrated in FIGS. 3a-d.

FIG. 3a illustrates a dressing 300, wherein the three dimensional features 309 are arranged in a discrete pattern 313 of "bean" shaped features across the surface of the backing layer 302.

FIG. 3b illustrates a dressing, wherein the three dimensional features 309 are arranged in a zig-zag pattern 314. Such a pattern may be particularly useful in embodiments where the dressing should be adapted to stretch more in the lateral (x) direction.

FIG. 3c illustrates a dressing, wherein the three dimensional features 309 are arranged in a discrete grid or "diamond" pattern.

FIG. 3d illustrates a pattern of discrete, circular three dimensional features 309.

The pattern of three dimensional features 309 extends over at least 30%, preferably at least 70%, more preferably at least 90% of the surface area of the backing layer (302).

As illustrated in FIGS. 3a-3d, the pattern is arranged to extend over the entire surface area of the backing layer 302.

This way, the flexibility is optimized, and the visual appearance of the dressing is further improved.

The dressing has a longitudinal (y) direction and a lateral (x) direction, and the three dimensional features 309 are arranged to extend in at least one of, preferably both of, the longitudinal (y) and the lateral (x) directions.

The flexibility of the dressing may be improved if the three dimensional features are arranged to extend in both the longitudinal (y) and the lateral (x) directions.

In alternative embodiments, the three dimensional features may be adapted to only extend, or extend significantly more, in one of the longitudinal (y) or the lateral (x) direction.

This may be beneficial for dressings adapted for pressure ulcer prevention purposes, e.g. a sacral dressing. For example, a bedridden patient at risk of developing pressure ulcers may need assistance from a caregiver to be repositioned in bed. This lateral movement may cause stress to the dressing and the backing layer, and the dressing should preferably be flexible in direction of movement when repositioned. In contrast, the dressing (and the backing layer) is preferably stiffer in the longitudinal direction.

The patterns of three dimensional features 309 also have the additional effect of improving the visual appearance of the dressing 300. A user may also be guided on how to apply the dressing correctly. For example, if the dressing is to be applied to a body part where stretching is particularly desired in one direction, the pattern may guide the user on how to apply the dressing to achieve this effect.

Figures 3E, 3F, 4:
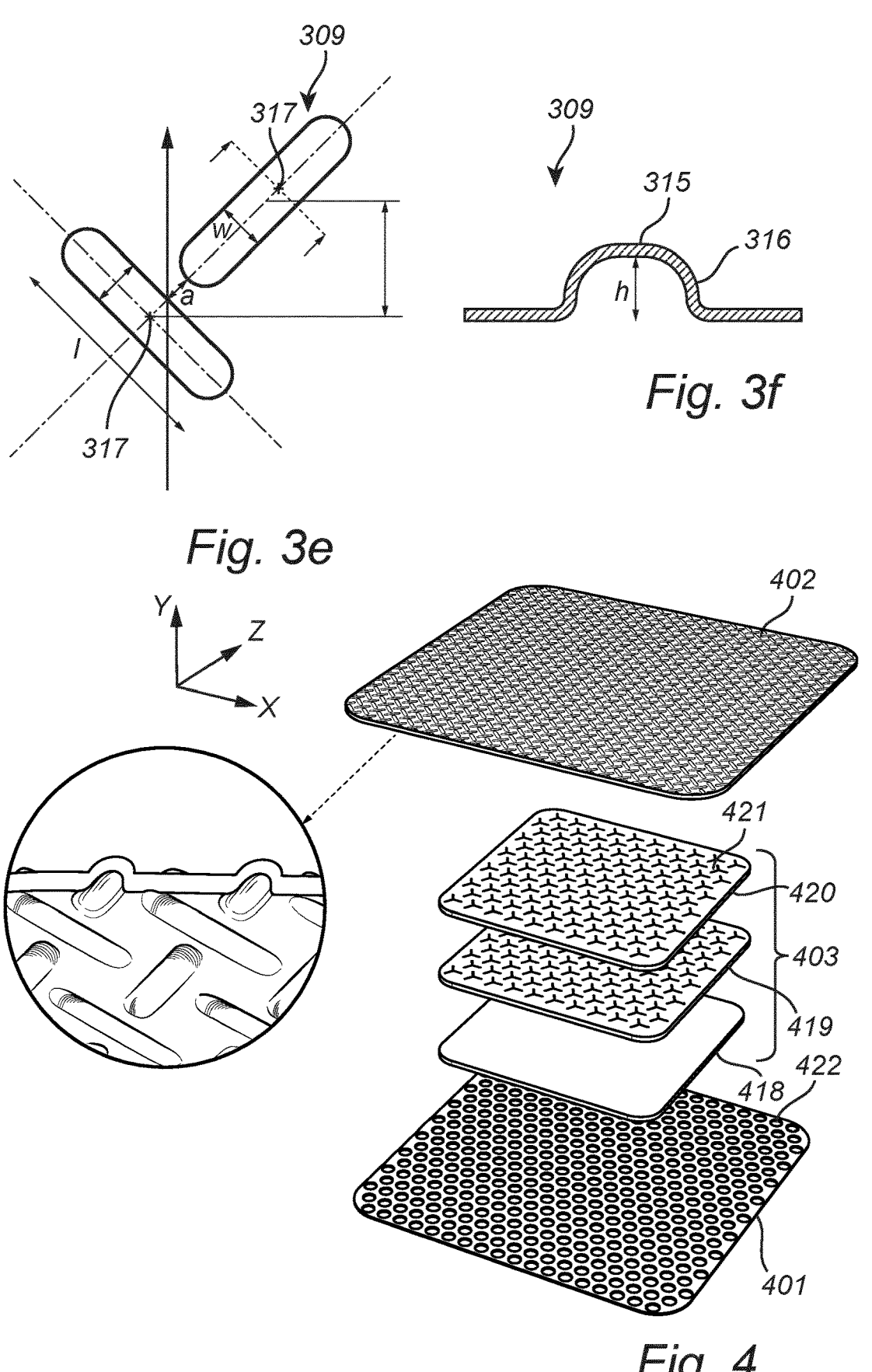

As illustrated in FIG. 3f, the three dimensional features 309 have a height, h, of between 0.3 and 10 mm, preferably between 0.5 and 5.0 mm, more preferably between 1.0 and 3.0 mm.

As used herein, the "height" refers to the maximal extension of the three dimensional feature in the z direction, and is measured from the from the top of one protrusion to the flat surface of the backing layer.

These dimensions are suitably used, and allow the backing layer 302 to stretch properly and conform to the body movement of the wearer.

The backing layer may have a non-uniform thickness. In other words, the backing layer comprises thinner material zones. The stretching ability is thereby improved, and accordingly, the wear time is enhanced. Furthermore, the breathability of the backing layer is improved, which is important for liquid handling.

The backing layer is typically thinner in the areas where the three dimensional features are arranged than in the areas of the backing layer being void of three dimensional features.

In embodiments, each three dimensional features 309 comprises a top portion 315, and at least one slope portion 316, wherein the thickness of the backing layer 302 in the top portion 315 of the three dimensional features 309 is higher than in the at least one slope portion 316 of the three dimensional features 309.

For example, the slope portion 316 may be at least 10% thinner, preferably at least 20% thinner, and more preferably at least 30% thinner than the top portion 315 of the three dimensional features 309.

This way, the flexibility and breathability of the backing layer is enhanced.

In embodiments, particularly where discrete three dimensional features are envisioned, the length-to-width ratio of each of the three dimensional features 309 may be at least 2:1, preferably at least 3:1.

The width and length of one protrusion are illustrated in FIG. 3e.

A suitable width, w, may be in the range of 0.5 mm-10 mm, e.g. 2 mm-5 mm.

A suitable length, l, may be in the range of 1 mm-20 mm, e.g. 4 mm-10 mm.

The length, l, and width, w, may be based, for instance, on the desired flexibility of the dressing and may also be varied depending on dressing size, and body part on which the dressing is to be applied.

The smallest space, a, between the three dimensional features may be at least 1 mm. For example, the space between the three dimensional features is between 2 mm and 15 mm. As illustrated in FIG. 3e, the smallest space, a, may e.g. be along a diagonal or oblique extension (relative to the longitudinal (y) and lateral (x) directions).

The space, a, between the three dimensional features depends on the height of the three dimensional features. For example, the space, a, may be larger if the height of the three dimensional features is large, and vice versa.

The discrete pattern may comprise three dimensional features arranged in rows of individual three dimensional features extending in the longitudinal (y) and lateral (x) direction of the dressing.

As illustrated in FIG. 3e, the center point 317 of each feature 309 may be offset from a center point of each feature in a neighboring row of three dimensional features. By offset is meant that the center points are not aligned and not arranged in parallel in respect of a line extending in the lateral (x) or longitudinal (y) directions and drawn between the center points 317 of three dimensional features arranged in a row.

The area occupied by the three dimensional features (309) may be e.g. 10-50%, preferably 20-40% of the total area of the backing layer.

FIG. 4 illustrates a dressing according to one embodiment of the present disclosure.

The dressing comprises a backing layer 402, a skin contact layer 401 and an absorbent pad 403 comprising three pad layers 418, 419 and 420.

The absorbent pad 403 comprises a plurality of cuts 421 extending at least partially through the absorbent pad. In FIG. 4, cuts 420 are provided in two of the pad layers 419 and 420, but it may be equally conceivable to only have cuts in one of the layers of the dressing.

The cuts 421, which may have various shapes, render the pad more flexible, and enhance the flexibility of the entire dressing.

The cuts 421 illustrated in FIG. 4 are provided as discrete groups of incisions, wherein each group of incisions comprises three incisions extending from a common starting point. The angle between the incisions may be between 40 and 150°. In FIG. 4, the angle between the incisions within one group 421 of incisions is 120°.

Accordingly, the pad or pad layer(s) is/are cut in both the longitudinal (y) and lateral (x) directions of the pad such that the pad becomes flexible in all directions In the various embodiments described hereinbefore, the backing layer may be a thin film, sheet or membrane that is vapor permeable. Examples of suitable materials for the backing layer include, but are not limited to polyurethane, polyethylene or polyamide films, silicone films, polyester based nonwoven materials, and laminates of polyester-based nonwoven materials and polyurethane films. Suitably, the backing layer is a polyurethane film having a thickness of from 5 to 40 μm, e.g. from 15 to 25 μm.

The pad according to the present disclosure may be formed from a single layer or multiple layers.

The pad may comprise a foam or a gel. It may also comprise a superabsorbent material e.g. superabsorbent polymers (SAP) or superabsorbent fibers (SAF).

For example, the absorbent pad may comprise two or more layers having different properties laminated together.

In embodiments, the absorbent pad comprises a first absorbent layer, a liquid acquisition layer, e.g. a nonwoven, and a second absorbent layer. The first absorbent layer may be a superabsorbent layer and the second absorbent layer may comprise an absorbent foam. Typically, the liquid acquisition layer is arranged between the first and the second absorbent layer, wherein the second absorbent layer is the lowermost layer of the absorbent pad. Suitable foam materials for use in the second absorbent layer include, but are not limited to polyurethane foams.

The superabsorbent layer may comprise a superabsorbent polymer (SAP) or superabsorbent fibers. A "superabsorbent polymer" or "SAP" is a polymer that can absorb up to 300 times its own weight in aqueous fluids. Superabsorbent polymers are constituted by water-swellable and water insoluble polymers capable of absorbing large quantities of fluid upon formation of a hydrogel. The superabsorbent polymers for use in accordance with the present disclosure may be inorganic or organic crosslinked hydrophilic polymers, such as polyvinyl alcohols, polyethylene oxides, crosslinked polyacrylates and the like. Typically, the superabsorbent (SAP) comprise sodium acrylate. The SAP material may be in the form of particles, fibers, flakes or similar.

The liquid distributing layer may comprise any material having the ability to distribute the exudate in an efficient manner. For example, the liquid distributing layer may comprise a nonwoven material. A nonwoven imparts an appropriately balanced rigidity to the layer and to the dressing as such. It may also efficiently distribute and spread liquid absorbed by the superabsorbent layer such that it can be evaporated through the backing layer over a large surface. For example, the nonwoven may comprise viscose, polyester or blends thereof.

The layers can be joined by adhesion, lamination, using pressure and heat.

The absorbent pad may comprise additional layers, such as liquid transport layers, various combinations of foam and nonwoven layers laminated together.

With reference to FIG. 4, the layer 418 comprises an absorbent foam, the layer 419 is a liquid acquisition layer, and the layer 420 is a superabsorbent layer.

Such a layered pad construction prevents accumulation of body liquids close to the skin.

The absorbent pad 403 may have a thickness in the range of from 1 to 10 mm.

Preferably, the thickness of the pad is in the range of from 2.5 to 6 mm, e.g. from 3 to 5 mm. The thickness of the absorbent pad 403 is measured in a dry condition.

In the various embodiments described, the term "skin contact layer" means a layer that is in contact with the skin of a wearer. The skin contact layer is adapted to adhere to the skin, which may or may not comprise a wound.

Preferably, the skin contact layer comprises a silicone based adhesive. Such an adhesive is skin-friendly and permits the removal of the dressing without causing damage to the skin.

Examples of suitable silicone gels include the two component RTV systems, such as Q72218 (Dow Corning), and SilGel 612 (Wacker Chemic AG) mentioned herein, as well as NuSil silicone elastomers. In embodiments of the invention the adhesive may comprise a soft silicone gel having a softness (penetration) of from 8 to 22 mm, e.g. from 12 to 17 mm, as measured by a method based on ASTM D 937 and DIN 51580, the method being described in European Patent Application No 14194054.4.

The skin contact layer may comprise one or several layers. In embodiments, the skin contact layer comprises a breathable polyolefin based film (e.g. polyethylene, polyamide, polyester, polyurethane) and a silicone adhesive layer.

The skin contact layer 401 may be perforated, as illustrated in FIG. 4. The perforations 422 typically extend through the skin contact layer 401. The perforations allow for a quick absorption into the pad 403 without compromising the tight fit to the skin provided by the adhesive layer. The perforations 422 may have different shapes and densities along varying regions of the skin contact layer 401, and may be arranged in a regular or irregular pattern.

The thickness ratio between the backing layer and skin contact layer is typically at least 1:2, preferably at least 1:3.

It is beneficial to have an even distribution of adhesive over the surface of the pad 403 in order to keep the dressing in place during use.

According to another aspect, the present disclosure relates to a method for forming a backing layer for a medical dressing; the backing layer comprising a plurality of three dimensional features, wherein the method comprises:
  providing a backing layer
  forming a plurality of three dimensional features in the backing layer by:
    a) heating the backing layer to a temperature between 100 and 200° C., preferably between 140 and 180° C. and
    b) contacting a first surface of the backing layer with a molding tool having a surface comprising a pattern of three dimensional structures.

Figure 5:
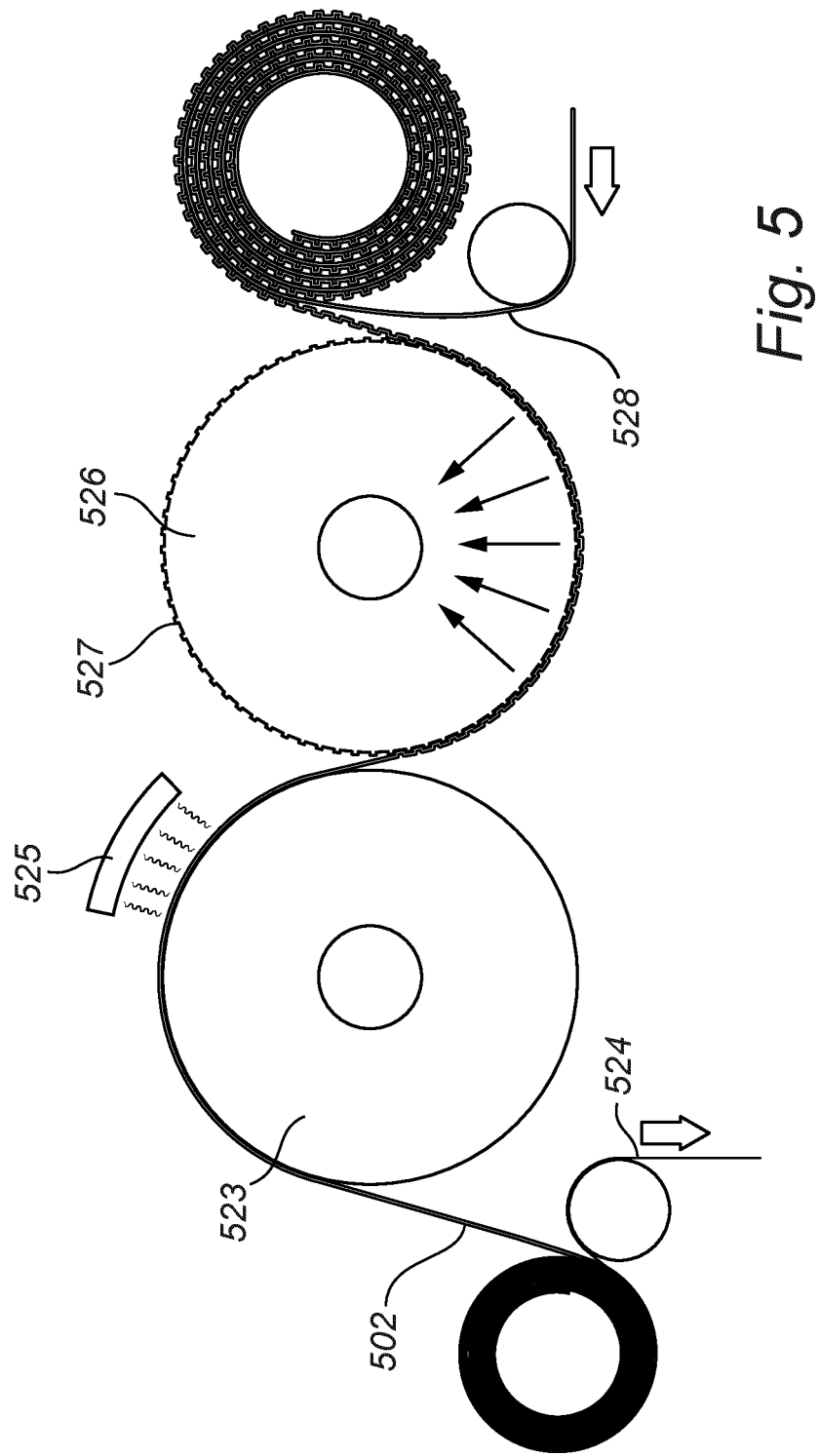
FIG. 5 illustrates a process for forming a backing layer according to the present disclosure.

FIG. 5 schematically illustrates the formation of such a backing layer, by means of a roll-to-roll process.

A backing layer 502 is fed onto a conveyor belt that transports the backing layer to a heating roll 523. Before heating, the backing layer 502 may be covered with a protective release layer 524, which is removed prior to heating. The surface of the heating roll 523 has a temperature between 100 and 200° C., preferably between 140 and 180° C., and the backing layer 502 is heated for a sufficient period of time, typically about 10-30 seconds, to almost reach its melting point. Alternatively, the heating of the backing layer may be achieved by irradiation from an infrared light source 525.

After heating, the backing layer 502, is transferred to a second roll, i.e. a molding tool 526 having a surface comprising a pattern of three dimensional structures 527.

This step b) is typically performed at a temperature between 10 and 50° C., preferably between 20 and 40° C. The backing layer 502 is thereby cured and affixed to the three dimensional structures 527 of the molding tool 526.

As illustrated by the arrows in FIG. 5, vacuum may be applied to the first surface of the backing layer. The vacuum source may be an integral part of the molding tool 526 or it may be an external vacuum source.

Preferably, the step b) and c) are performed simultaneously.

The vacuum application enhances the fixation of the three dimensional features in the backing layer 502. It also stretches the backing layer 502 such that a non-uniform thickness is obtained. Stretching of the backing layer while simultaneously contacting the surface of the backing layer with a structured molding tool 526 results in three dimensional features comprising slope portions being thinner than the corresponding top portions of the features.

When the three dimensional features have been affixed in the backing layer 502, the backing layer may be covered with a protective release layer 528 and stored before assembly with the remaining components of the dressing.

The time required to affix the three dimensional features in the backing layer is typically about 1-10 seconds and depends on the temperature of the molding tool 526; i.e. when the backing layer 502 has reached room temperature after the heating step.

The backing layer may subsequently be arranged onto an adhesive skin contact layer, or onto an absorbent pad, if present.

The process of the present disclosure is not limited to the use of a roll-to-roll process. Any technique for heating the film may be used. The molding tool may be any tool from which a structured pattern can be generated, and is not limited to a cylindrical roll as illustrated in FIG. 5. For example, a planar stamping press, or any other embossment tool may be utilized.

According to another aspect, there is provided a method for forming a medical dressing comprising:

providing a backing layer comprising a plurality of three dimensional features, arranging the backing layer on an adhesive skin contact layer, optionally arranging an absorbent pad between the backing layer and the skin contact layer, wherein the backing layer has a first surface facing the skin contact layer and an opposing second surface, and wherein the plurality of three dimensional features are formed by a) heating the backing layer to a temperature between 100 and 200° C., preferably between 140 and 180° C. and b) contacting the first surface of the backing layer with a molding tool having a surface comprising a pattern of three dimensional structures.

The steps and features of the process for forming a backing layer described above are also applicable for the method for forming a medical dressing.

Example 1: Evaluation of the Wear Time

In order to evaluate the effect of the dressing according to the present disclosure, the wear time was evaluated and compared with reference dressings.

In a first test set-up, four different types of dressings were prepared for comparative analysis. The dressings all had a similar construction, but differed with respect to the backing layer, and with respect to the thickness of the absorbent pad.

The reference dressings (dressings C and D) comprised a skin contact layer; i.e. a 20 μm perforated (13% open surface area) polyurethane film coated with 200 gsm of silicone gel adhesive, an absorbent pad made of polyurethane foam (3.3 mm and 5.2 mm, respectively). The backing layer was made of a 20 μm polyurethane plastic (flat) film. Acrylic adhesive was used to assemble the dressing, i.e. to attach the backing layer to the absorbent pad and border portion of the skin contact layer. The size of each dressing was 10×10 cm with a wound pad 6.5×6.5 cm in a central position.

The dressings according to the present disclosure (dressings A and B) differed from the reference dressings in that the backing layer was embossed using a vacuum machine, Formech 300XQ, at 150-180° C. Vacuum and heat was applied and the backing layer brought in contact with a metallic net having threads of 0.9 mm diameter and a distance of 3 mm between each thread. The pattern of three dimensional features of the backing layer for dressings A and B was that illustrated in FIG. 3a. The metallic net had a corresponding structured pattern, and with respect to the parameters defined in FIG. 3e, each "bean" had a width, w, of 1.0 mm and a length, l, of 3.5 mm. The distance, a, between the bean shaped structures was 1.0 mm.

The following dressings were tested:

Dressing A: Inventive dressing with an absorbent pad thickness of 3.3 mm

Dressing B: Inventive dressing with an absorbent pad thickness of 5.2 mm

Dressing C: Reference dressing with an absorbent pad thickness of 3.3 mm

Dressing D: Reference dressing with an absorbent pad thickness of 5.2 mm

Figure 6:
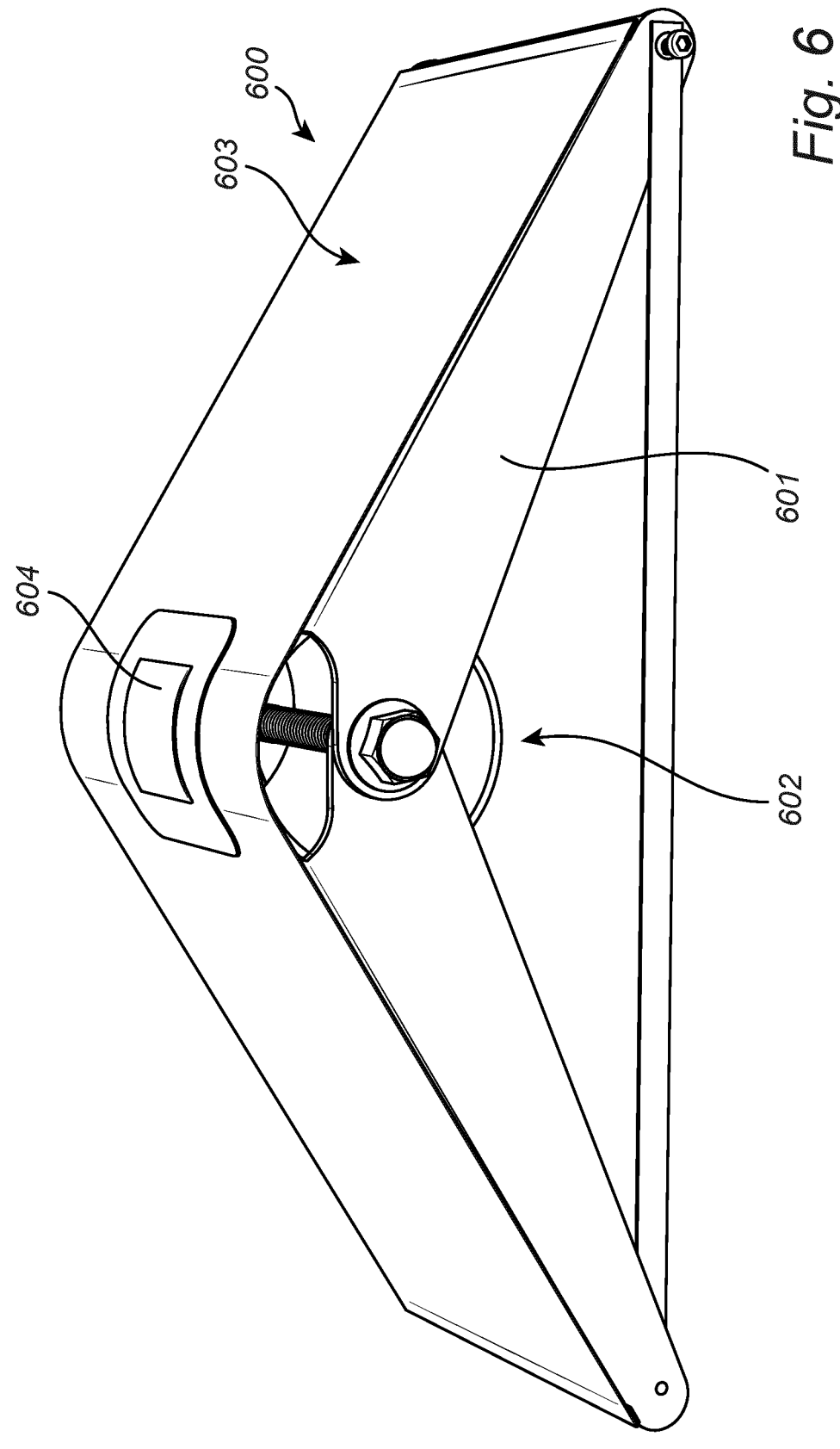
FIG. 6 illustrates the test equipment used for evaluating the wear time of the dressings of the present disclosure compared to reference dressings.

FIG. 6 illustrates the test equipment that was used for the wear time evaluation.

The test equipment 600 was a plastic plate 601 with a cylinder hinge 602 of a size to mimic an articulating joint, e.g. a knee (80 mm in diameter). A polyurethane plastic film 603 was attached to the upper surface of the plate 601 to mimic the skin. When the dressings 604 were applied, the deviation in angle from the horizontal plane was approximately 10 degrees. As a next step, the plate 601 was inclined by attaching a strap and the deviation from the horizontal plane was now approximately 55 degrees. Time (in seconds) was then measured from when the dressing 604 was applied until at least a part of the border portion of the dressing started detaching from the film 603. Five different sets of dressings (A-D) were tested and the results are illustrated in Table 1 below, wherein the time is an average of each dressing set.

TABLE 1

| Time before dressing started detaching | |
| --- | --- |
| Dressing sample | Time (s) |
| Dressing A | 378 |
| Dressing B | 166 |
| Dressing C | 78 |
| Dressing D | 39 |

As illustrated in table 1, the wear time was significantly improved with the dressings according to the present disclosure.

Figure 8:
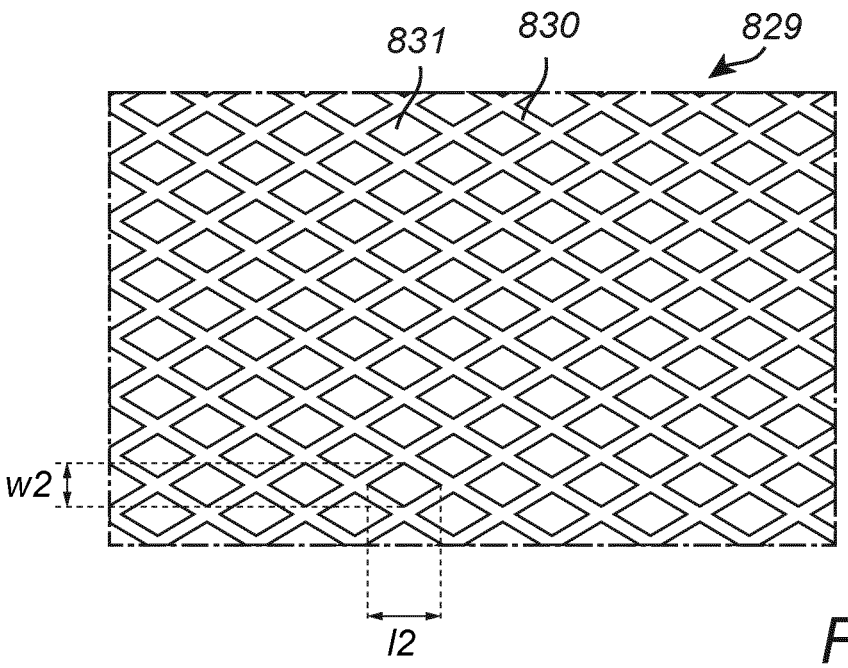
FIG. 8 illustrates the metallic net utilized for construction of the pattern of three dimensional features of FIG. 3c.

In the second test set-up, two additional dressings (dressing E and F) according to the present disclosure, were tested. Dressing E had the same construction as Dressing B and D above (5.2 mm foam pad), but differed with respect to the pattern of three dimensional features in the backing layer. The pattern of three dimensional features for the backing layer of dressing E was the pattern illustrated in FIG. 3c. The backing layer was embossed using a vacuum machine, Formech 300XQ, at 150-180° C. Vacuum and heat was applied and the backing layer was brought in contact with a metallic net 829 as illustrated in FIG. 8. The diameter of the threads 830 was 1.0 mm, the width, w2, of each "diamond" 831 in the net pattern was 6.0 mm, and the length, l2, was 10 mm. The depth of each diamond (corresponding to the height of the three dimensional feature to be formed) was 1.2 mm. Dressing F had the same pattern of three dimensional features as Dressing E, but differed with respect to the construction of the absorbent pad. The pad comprised three different layers; i.e. from bottom-to-top: a polyurethane foam layer, a nonwoven layer and a superabsorbent layer). The superabsorbent layer and the nonwoven layer comprised cuts in accordance with layer 420 in FIG. 4 (where the cuts are illustrated as 421). The thickness of the absorbent pad of Dressing F was about 5 mm.

The same test equipment as used in the first test-up (illustrated in FIG. 6) was utilized to evaluate the wear time of the dressings. Eight samples of Dressing E were tested and three samples of Dressing F were tested, wherein Table 2 below summarizes the average time (in seconds) until at least part of the border portion started detaching.

TABLE 2

| Time before dressing started detaching | |
| --- | --- |
| Dressing sample | Time (s) |
| Dressing E | 399 |
| Dressing F | >600 |

As illustrated in table 2, the wear time was significantly improved with the dressings according to the present disclosure. The tests were stopped after 600 seconds, wherein Dressing F was still completely attached, with no signs of detachments. This may be attributed to a synergetic effect of inducing flexibility in both the wound pad (by means of the cuts in the pad-forming layer) and the backing layer (by means of the three dimensional features).

Example 2: Evaluation of Moisture Vapor Transmission

In order to evaluate the effect of the dressings according to the present disclosure, the moisture vapor loss though the backing layer was evaluated and compared with reference dressings.

Three different dressings were used for comparative analysis (Dressing F, G and H). Dressing F had the construction as defined hereinbefore. All dressings (F, G and H) had a similar construction, but differed with respect to the backing layer (see above with respect to the construction of dressing F). The backing layer of dressing H (reference dressing) comprised a 20 μm polyurethane film (a flat layer). The backing layer of inventive dressing F comprised a 20 μm polyurethane film with a pattern of three dimensional features as illustrated in FIG. 3c (diamond shaped three dimensional features), and the backing layer (a 20 μm polyurethane film) of dressing G had a pattern of three dimensional features as illustrated in FIG. 3d (circular three dimensional features). The patterns of three dimensional features were formed with the same machine equipment as explained hereinbefore. The metallic net utilized for forming the circular protrusion comprised circular structural features having a diameter of 4.7 mm, wherein the distance between the center of once circle to a neighboring circle was 6.7 mm. The depth of each circle (corresponding to the height of the three dimensional feature to be formed) was 2.0 mm.

Figure 7:
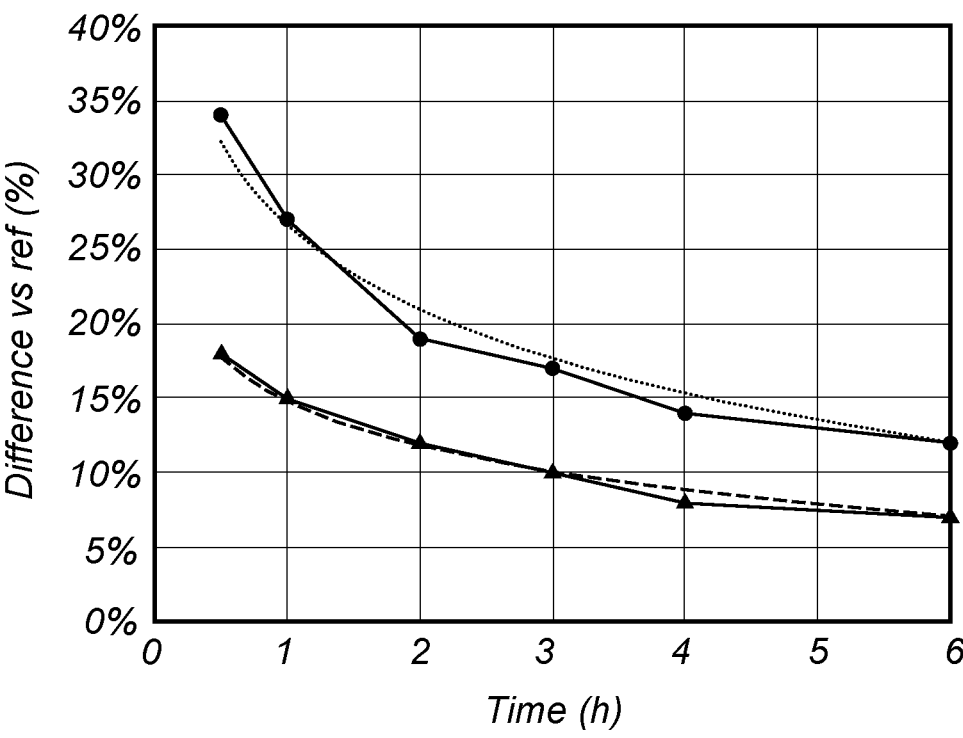
FIG. 7 illustrates the improvement in moisture vapor transmission through the backing layer of two dressings according to the present disclosure compared to a reference dressing.

In order to test the moisture vapor loss through the backing film, each product sample was placed on a transparent plastic paper (having a size of approximately 12×16 cm). The dry samples and the plastic paper were weighed ($W_1$). The plastic paper was removed after weighing and approximately 20 ml of liquid (tap water) was added to the product, through the skin contact layer. The liquid was added to the product by means of a plexiglas tube (having a length of 75 mm and inside diameter of 16 mm) attached to a circular plate (having a thickness of 11 mm and a diameter of 71 mm). The circular plate was used to form an even surface against the skin contact layer of the dressing and to secure an even distribution of liquid across the pad. The circular plate comprising the Plexiglas tube was positioned centrally on each dressing prior to liquid addition. The liquid was allowed to enter the wound pad such that the pad became homogenously wet. To secure that all dressings had the same wet surface area, the dressings were slightly massaged. The plastic papers were re-applied and the wet product samples (including the plastic paper) were weighed again ($W_2$). Subsequently, the product samples were placed on a heating plate. After 30 minutes, the samples were removed and re-weighed (including the plastic paper) ($W_3$). The samples were placed back on the heating plate and the samples were re-weighted after each 30 or 60 minutes. The mass of moisture vapor loss through the backing film ($W_X$–$W_1$) was calculated. FIG. 7 illustrates the improved moisture vapor transmission with the inventive dressings compared to a reference over time. FIG. 7 shows the average of five dressings in each dressing set of the inventive dressings F and G.

As illustrated in FIG. 7, the moisture vapor transmission through the backing layer is significantly improved with the inventive dressings.

Terms, definitions and embodiments of all aspects of the present disclosure apply mutatis mutandis to the other aspects of the present disclosure.

Even though the present disclosure has been described with reference to specific exemplifying embodiments thereof, many different alterations, modifications and the like will become apparent for those skilled in the art.

Variations to the disclosed embodiments can be understood and effected by the skilled addressee in practicing the present disclosure, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A medical dressing comprising:

an adhesive skin contact layer;

a backing layer; and an absorbent pad having a skin-facing surface and an outwardly facing surface opposite the skin-facing surface, wherein the absorbent pad is arranged between said backing layer and said adhesive skin contact layer so that the skin-facing surface faces the adhesive skin contact layer and the outwardly facing surface faces the backing layer, wherein said backing layer has a first surface facing said adhesive skin contact layer and an opposing second surface, characterized in that said backing layer comprises a plurality of three dimensional features forming protrusions on said second surface of said backing layer and depressions on said first surface of said backing layer, wherein said depressions of said backing layer define gaps between an immediately adjacent underlying layer that is one of said adhesive skin contact layer or said absorbent pad, wherein a first area of the backing layer overlies an entirety of the absorbent pad, and wherein the backing layer is a continuous and uninterrupted surface across an entirety of the first area.

2. The medical dressing according to claim 1, wherein each three dimensional feature comprises a top portion, and at least one slope portion, wherein, for each three dimensional feature, a thickness of the backing layer in said top portion of each three dimensional feature is greater than in said at least one slope portion of said three dimensional feature.

3. The medical dressing according to claim 2, wherein, for each three dimensional feature, each slope portion of said at least one slope portion is at least 10% thinner than said top portion of each three dimensional feature.

4. The medical dressing according to claim 3, wherein said absorbent pad comprises a plurality of cuts extending at least partly through said absorbent pad.

5. The medical dressing according to claim 1, wherein said three dimensional features are arranged in a discrete or continuous pattern across at least a portion of said backing layer.

6. The medical dressing according to claim 5, wherein said pattern of three dimensional features extends over at least 30% of the surface area of said backing layer.

7. The medical dressing according to claim 1, wherein said adhesive skin contact layer is substantially planar.

8. The medical dressing according to claim 1, wherein said backing layer and said adhesive skin contact layer extend around the periphery of said absorbent pad, wherein said first surface of said backing layer is not adhesively attached to said absorbent pad in the areas forming said depressions.

9. The medical dressing according to claim 1, wherein said dressing has a longitudinal (y) direction and a lateral (x) direction, and wherein said three dimensional features are arranged to extend in at least one of said longitudinal (y) and said lateral (x) directions.

10. The medical dressing according to claim 1, wherein said three dimensional features have a height of between 0.3 and 10 mm.

11. The medical dressing according to claim 1, wherein said backing layer has a non-uniform thickness.

12. The medical dressing according to claim 1, wherein the absorbent pad as a periphery, wherein the backing layer extends beyond the periphery of the absorbent pad to define a border portion, wherein the plurality of the three dimensional features overlie the absorbent pad and the border portion.

13. The medical dressing according to claim 1, wherein the absorbent pad has a periphery, wherein the backing layer extends beyond the periphery of the absorbent pad to define a border portion, wherein the adhesive skin contact layer extends beyond the periphery of the absorbent pad and contacts the backing layer within the border portion.

14. A medical dressing comprising:

an adhesive skin contact layer;

a backing layer, wherein said backing layer has a first surface facing said adhesive skin contact layer and an opposing second surface, characterized in that said backing layer comprises a plurality of three dimensional features forming protrusions on said second surface of said backing layer and depressions on said first surface of said backing layer; and an absorbent pad having a skin-facing surface and an outwardly facing surface opposite the skin-facing surface, wherein the absorbent pad is arranged between said backing layer and said adhesive skin contact layer so that the skin-facing surface faces the adhesive skin contact layer and the outwardly facing surface faces the backing layer, wherein said first surface of said backing layer is not attached to either of said adhesive skin contact layer or said absorbent pad in areas forming said depressions, wherein a first area of the backing layer overlies an entirety of the absorbent pad, and wherein the backing layer is a continuous and uninterrupted surface across an entirety of the first area.

15. The medical dressing according to claim 14, wherein said depressions of said backing layer provide gaps between an underlying one of said adhesive skin contact layer or said absorbent pad.

* * * * *